US00PP26154P2

(12) United States Plant Patent
Fraser

(10) Patent No.: US PP26,154 P2
(45) Date of Patent: Nov. 24, 2015

(54) ***CORDYLINE* PLANT NAMED 'SALSA'**

(50) Latin Name: *Cordyline australis*
Varietal Denomination: Salsa

(71) Applicant: Peter Fraser, Kihikihi Te Awamutu (NZ)

(72) Inventor: Peter Fraser, Kihikihi Te Awamutu (NZ)

( * ) Notice: Subject to any disclaimer, the term of this patent is extended or adjusted under 35 U.S.C. 154(b) by 136 days.

(21) Appl. No.: 13/998,337

(22) Filed: Oct. 22, 2013

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Keith O. Robinson

(57) ABSTRACT

A new cultivar of *Cordyline* plant named 'Salsa' that is characterized by leaves that are linear in shape, initially erect then outwardly arching and dark red-purple in color with a pink midrib and pink margins.

1 Drawing Sheet

Botanical classification: *Cordyline australis.*
Variety denomination: 'Salsa'.

BACKGROUND OF THE INVENTION

The present invention relates to a new and distinct cultivar of *Cordyline australis* and is hereinafter referred to by the cultivar name 'Salsa'. The new cultivar was discovered by the inventor in a cultivated area of Kihikihi, Te Awamutu, New Zealand in 2007. The new cultivar was discovered as a single plant in a population of seed grown unidentified *Cordyline australis* cultivars. 'Salsa' was discovered in an indoor greenhouse. The exact parent plants are unknown.

The new cultivar was first asexually propagated by tissue culture in Auckland, New Zealand in 2010. Since that time, under careful observation, the unique characteristics of the new cultivar have been uniform, stable and reproduced true to type in successive generations of asexual reproduction.

SUMMARY OF THE INVENTION

The new *Cordyline* 'Salsa' is distinguished from other known varieties of *Cordyline,* by the following characteristics:

1. *Cordyline* 'Salsa' exhibits leaves that are initially erect then outwardly arching.
2. *Cordyline* 'Salsa' exhibits linear shaped leaves
3. *Cordyline* 'Salsa' exhibits dark red-purple leaves with a pink midrib and pink margins.

The closest comparison cultivar is *Cordyline* 'Midnight Star' (not patented). 'Salsa' is distinguishable from 'Midnight Star' in having wider leaves and variegated leaves that are dark red-purple with a pink midrib and pink margins. In comparison, the leaves of 'Midnight Star' are brown with a grey-orange midrib. The leaves of 'Salsa' are larger in width than the leaves of 'Midnight Star'.

BRIEF DESCRIPTION OF THE DRAWINGS

The accompanying color photograph illustrates the distinguishing characteristics of the new cultivar 'Salsa'.

The photograph shows an overall view of a 2 year old plant.

All photographs are taken using conventional photographic techniques and although foliage colors may appear different from actual colors due to light reflectance, they are as accurate as possible by conventional photography.

BOTANICAL DESCRIPTION OF THE PLANT

The following is a detailed description of the *Cordyline* cultivar named 'Salsa'. Data was collected in Kihikihi, Te Awamutu, New Zealand from 2 year old plants. The plants were grown outdoors in 2.5 liter containers under 30 percent shade house cover. The time of year was Spring in the Southern Hemisphere. Phenotypic differences may be observed with variations in environmental, climatic, and cultural conditions, without however, any difference in genotype. Color determinations are in accordance with The 2001 Royal Horticultural Society Colour Chart except where general color terms of ordinary dictionary significance are used. The growing requirements are similar to the species.

Botanical classification: *Cordyline australis* 'Salsa'.
Common name: Cabbage Tree.
Parentage: The exact parent plants of 'Salsa' are unknown.
Type: Ornamental perennial.
Growth rate: 5 cm. per month.
Overall shape: Upright to semi-erect, broadly inverted triangle.
Habit: Upright, arching.
Height: Average 1.1 m. in height.
Spread: Average 1.3 m. in width.
Low temperature tolerance: –3 degrees Centigrade.
High temperature tolerance: 35 degrees Centigrade.
Propagation method: Tissue Culture.
Time to initiate roots: 6 months.
Time to produce a rooted liner: 2 months.
Crop time: 14 months.
Vigor: Moderate.
Root system: Fine and fibrous.
Root color: N155.
Stem:
*Texture.*—Smooth.
*Dimensions.*—Average 3.8 cm. in diameter and 5.1 cm. in length.

*Color*.—N199A.

Foliage:

*Arrangement*.—Whorled.

*Orientation*.—Initially erect then outwardly arching.

*Average number of leaves per plant*.—48.

*Compound or single*.—Single.

*Leaf attachment*.—Sessile.

*Leaf shape*.—Linear.

*Leaf dimensions*.—Average 50 cm. in length and 20 mm. in width.

*Leaf apex*.—Acute.

*Leaf base*.—Attenuate.

*Leaf margins*.—Entire.

*Leaf texture*.—Upper and lower surfaces: Smooth.

*Leaf glossiness*.—Upper and lower surfaces: Medium.

*Leaf color of young leaves* (*upper surface*).—187A, midrib 59C and margins 60A.

*Leaf color of young leaves* (*lower surface*).—59B, midrib 184B and margins 184C.

*Leaf color of mature leaves* (*upper surface*).—187A, midrib 59C and margins 60A.

*Leaf color of mature leaves* (*lower surface*).—59B, midrib 184B and margins 184C.

*Venation pattern*.—Parallel.

*Vein color* (*upper surface*).—59C.

*Vein color* (*lower surface*).—184B.

*Pinching*.—Removal of young plant tips is not required.

*Durability of foliage to stress*.—High.

*Leaf fragrance*.—Absent.

Flower production: No flowers have been produced by 'Salsa' to date.

Fruit and seed production: No fruit or seed has been produced by 'Salsa' to date.

Disease and pest resistance: Has not been observed.

The invention claimed is:

1. A new and distinct variety of *Cordyline* plant named 'Salsa' as described and illustrated.

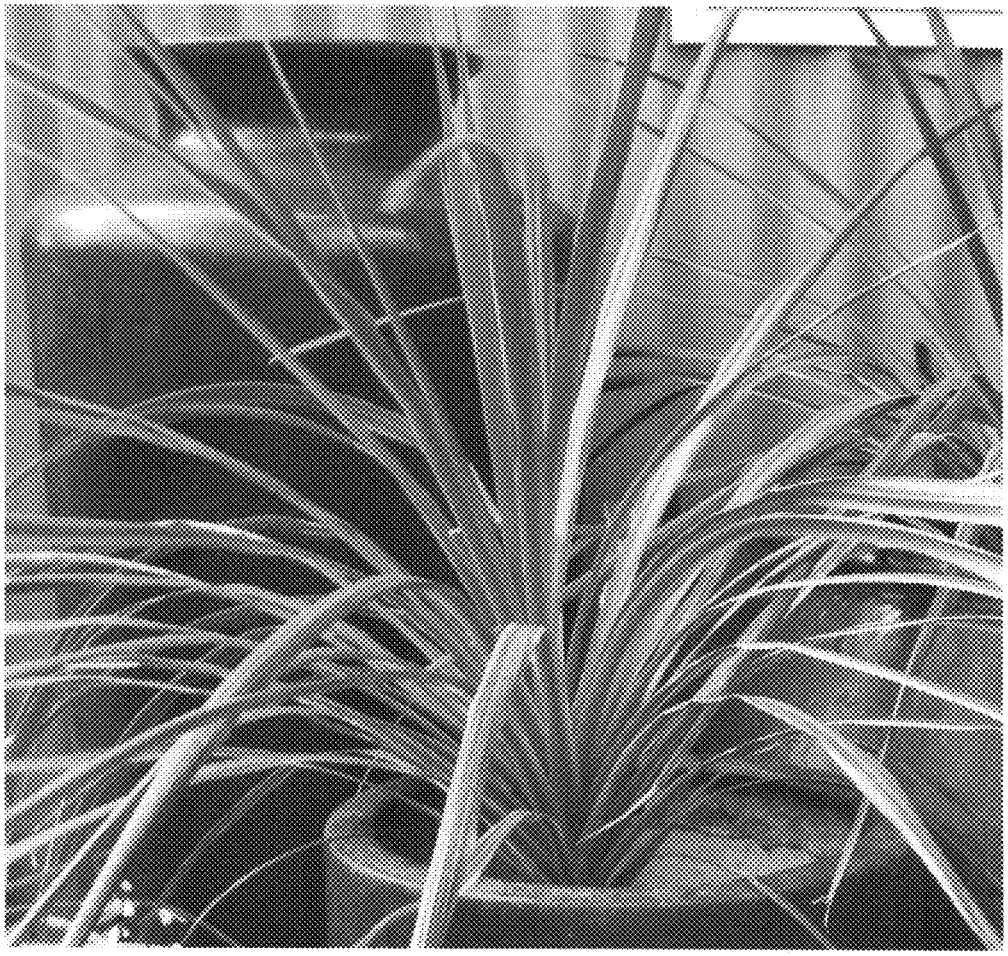

* * * * *